United States Patent [19]

Oldham et al.

[11] Patent Number: 5,766,632
[45] Date of Patent: Jun. 16, 1998

[54] METHOD OF USING LECTINS FOR CONTRACEPTION

[75] Inventors: Michael J. Oldham. Oxnard; Bruce F. Rose. Ventura. both of Calif.

[73] Assignee: Legere Pharmaceuticals, Ltd.. Carson City. Nev.

[21] Appl. No.: 609,980

[22] Filed: Feb. 29, 1996

Related U.S. Application Data

[60] Continuation of Ser. No. 462,664, Jun. 5, 1995, abandoned, which is a division of Ser. No. 317,599, Oct. 3, 1994, which is a continuation-in-part of Ser. No. 130,190, Oct. 1, 1993, abandoned.

[51] Int. Cl.$^6$ .................. A61K 91/14; A01N 37/18
[52] U.S. Cl. .................. 424/486; 424/DIG. 14; 514/2; 514/841; 514/843; 514/953; 514/967
[58] Field of Search .................. 424/486, DIG. 14; 514/2. 967. 953. 841. 843

[56] References Cited

U.S. PATENT DOCUMENTS

| | | | |
|---|---|---|---|
| 4,585,615 | 4/1986 | Beck et al. | 424/88 |
| 5,077,198 | 12/1991 | Shih et al. | 435/7.9 |

Primary Examiner—Nathan M. Nutter
Attorney, Agent, or Firm—Vorys. Sater. Seymour & Pease

[57] ABSTRACT

In order to prevent conception and/or the spread of sexually transmitted diseases (STD's) one or more lectins capable of binding sperm and/or the pathogenic microorganisms responsible for STD's are administered to the vagina prior to sexual intercourse. The lectins immobilize the sperm to render them incapable of fertilization and also bind to the microorganisms to render them non-pathogenic or to the cells to prevent infection by the microorganisms. Lectins can also be administered to treat sexually transmitted vaginal infections. The invention also encompasses a device for to be placed in the vault of the vagina which comprises a ring which surrounds the cervix and a membrane spanning the central aperture of the ring to prevent the direct contact of ejaculate with the cervical tissues. The device is impregnated or coated with lectins and releases them into the vaginal environment over a period of time.

4 Claims, 2 Drawing Sheets

METHOD OF USING LECTINS FOR CONTRACEPTION

This is a continuation of Ser. No. 8/462,664 filed on Jun. 05, 1995, which is a divisional of application Ser. No. 08/317,599, filed Oct. 03, 1994, which is a continuation-in-part of application Ser. No. 08/130,190, filed Oct. 01, 1993, now abandoned.

BACKGROUND OF THE INVENTION

1. Field of the Invention

This invention relates generally to methods of contraception and prophylaxis against diseases transmittable by sexual contact and therapy of such diseases, and more particularly to a method using intravaginally administered lectins for contraception and to protect against the transmission of diseases that are transmissible by sexual contact and to treat such diseases. The invention also relates to devices for intravaginal administration of lectins.

2. Brief Summary of the Prior Art

Sexually transmitted diseases (STD's) are epidemic in this country and worldwide. Furthermore, other diseases that have not traditionally been considered to be STD's have also been found to be transmitted by sexual contact, e.g., hepatitis B. The medical and public health problems associated with these epidemics have motivated a search for methods of controlling these diseases by limiting their transmission from person to person. Similarly, although many methods of contraception have been employed, no universally satisfactory method has been developed.

Hitherto it has been generally agreed that barrier methods which prevent the contact of body fluids between individuals are the most effective means of preventing transmission of such diseases. Such barrier methods are also effective contraceptive procedures. However, such methods are somewhat inconvenient and require some cooperation between individuals.

An alternative method for preventing the transmission of sexually transmitted diseases is to kill the pathogenic microorganisms in semen and vaginal secretions so that they are incapable of invading the tissues and causing the disease. While intravaginally placed spermatocides have been used for contraception, alone or in combination with barrier methods, antimicrobial materials have not been so used to prevent STD's, probably because many of such materials are irritating to adjacent tissues.

Administration of biologically active materials to the vagina for whatever purpose is usually accomplished by the use of some device that provides for convenient application of the medication by the user herself. A variety of devices exist for delivery of bioactive substances such as spermatocides and various medications. Each has its place in the medical armamentarium but each has certain deficiencies for application of contraceptive or anti-microbial agents in the context of sexual activity. Conventional vaginal suppositories and ovules may not provide medication to the entire vagina because of their shape and placement by the user in the vagina. Such suppositories are generally comprised of a material that melts at body temperature to allow the medication to spread and contact the tissues. However, when the dosage form melts, the medication may drain out of the vagina rather quickly, thus minimizing its potential effectiveness and significantly reducing the extended exposure of the tissues and pathogens to the medication which is often necessary for effective treatment. Similarly, the effective duration of contraceptives applied in this way tends to be relatively brief. In addition, such delivery vehicles, even when freshly applied, do not provide any physical barrier to deposition of male ejaculate on the cervix. Such ready access of sperm to the cervix may allow them to escape the action of spermatocides that are diffused throughout the vagina. Furthermore, because cells at the cervix are uniquely sensitive to several pathogens such as *Chlamydia trachomatis*, the absence of a barrier deprives these cells of a significant means of protection.

In order to provide for a longer retention of medication in the vagina and assure a more continuous delivery of active ingredients to the tissue, several types of vaginal rings have been proposed. Such devices are disclosed, for example, in Duncan, U.S. Pat. No. 3,545,439; Roseman, U.S. Pat. No. 3,920,805; Schopflin, U.S. Pat. Nos. 4,012,496 and 4,012,497; Wong et al., U.S. Pat. Nos. 4,237,885 and 4,286,587; and Nash et al., U.S. Pat. No. 4,292,965. The vaginal rings are generally impregnated with a spermatocide and are designed to be retained in the vaginal vault and to release the spermatocide slowly over a period of time to maintain an effective contraceptive concentration of the active material in the vagina. However, such devices do not prevent the direct contact of ejaculate with the tissues of the cervix, and therefore do not protect those tissues from contact with pathogenic organisms which might be contained in the ejaculate. They are also of questionable efficacy in supplying the spermatocide where it is most needed.

Another approach is to use a cervical cap or a diaphragm to serve as a mechanical barrier to the sperm and to dispense medication. These devices are designed for a relatively tight fit either to the cervix or the walls of the vagina to serve as a mechanical barrier to the passage of sperm. Such devices can be effective, especially as contraceptives and when combined with spermatocides. However, because of the need to provide a sperm-resistant seal they are frequently relatively complex devices incorporating metallic springs within a rubber or synthetic resin structure to provide the required sealing force.

Another approach to providing an effective concentration of spermatocide in the vagina is to provide a sponge impregnated with a spermatocide. Such applicators are not intended to be precisely located and may permit the contact of ejaculate with the tissues of the cervix, with the undesirable consequences outlined above.

Accordingly, a need has continued to exist for a method of contraception and prophylaxis against STD's by vaginal administration of a spermatocide and/or antimicrobial material, and for a simple and effective device to protect the tissues at risk from contact with microorganisms while dispensing a spermatocidal and/or antimicrobial material.

SUMMARY OF THE INVENTION

This need has now been alleviated by the method and device of this invention, according to which one or more lectins capable of binding sperm and/or the pathogenic microorganisms responsible for STD's are administered to the vagina or site of infection prior to sexual intercourse. The lectins immobilize sperm to render them incapable of fertilization and also bind to the microorganisms to render them non-pathogenic or to the cells to prevent infection by the microorganisms.

The invention also encompasses a device for to be placed in the vault of the vagina which comprises a ring which surrounds the cervix and a membrane spanning the central aperture of the ring to prevent the direct contact of ejaculate with the cervical tissues. The device is impregnated or coated with lectins and releases them into the vaginal environment over a period of time.

Accordingly, it is an object of the invention to provide an improved method for prophylaxis against sexually transmitted diseases.

A further object is to provide a method of contraception.

A further object is to provide a method for binding and immobilizing pathogenic microorganisms in the vagina.

A further object is to provide a method for treating vaginal infections.

A further object is to provide a device for delivering lectins to the vagina over a period of time.

A further object is to provide an intravaginal device that protects the tissues of the cervix from direct contact with ejaculate.

Other objects of the invention will become apparent from the following detailed description when considered in conjunction with the drawings.

DETAILED DESCRIPTION OF THE INVENTION AND PREFERRED EMBODIMENTS

Figure 1:
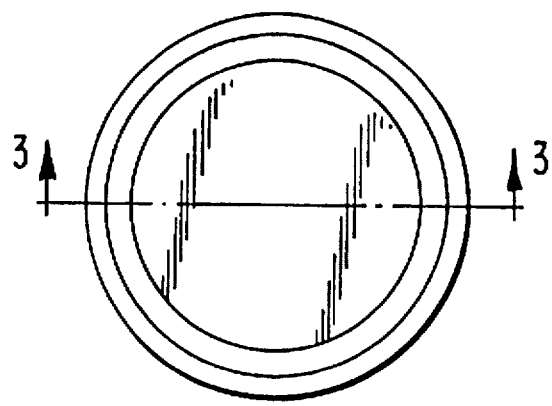
FIG. 1 is a top plan view of a lectin-delivery device according to the invention.

Lectins are carbohydrate-binding proteins of nonimmune origin that agglutinate cells or precipitate polysaccharides or glycoconjugates, i.e., proteins or lipids conjugated to oligo- or polysaccharides. They are widely distributed, and have been isolated from both plant and animal sources. Their reactions with living cells are based on their ability to bind with antibody-like specificity to particular arrangements of the sugar residues that make up oligo- or polysaccharides.

The surface of eucaryotic cells contain very numerous molecules of glycoproteins and glycolipids. Similarly, the cell walls of bacteria and the envelopes and capsids of viruses contain structural polysaccharides and/or glycoproteins. The carbohydrate moieties of these molecules which are displayed on the cell surfaces exhibit great variety in composition and structure that serves to distinguish the types of cells and to serve as a signal to other cells or materials which come into contact with the cell. For, example, variation in the carbohydrate moieties of glycoproteins in the membrane of red blood cells serves as the basis for the conventional blood typing classification. When lectins recognize and bind to certain carbohydrate moieties they may serve to cross-link and agglutinate the cells bearing the binding groups, a property that earns for them the alternate name of agglutinins. Furthermore, because the same sort of carbohydrate moieties often serve as attachment points for pathogens to bind to target cells and invade them, lectins may block infection of target cells by blocking the sites used by pathogens as recognition markers. The same type of specific binding occurs between sperm and egg in conception, and can be blocked by lectins. The binding ability of lectins may be very specific for certain mono- or oligosaccharides, allowing lectins to be used as a powerful tool for investigating the oligosaccharide epitopes on the surface of organisms or cells. Lectins can distinguish between blood cells of specific blood type, malignant from normal cells, and among species and genus of organisms. While glycoproteins, glycolipids, and bacterial cell walls are believed to be the main lectin-binding locations on the surface of cells, it is not excluded that carbohydrate moieties derived from other molecules or cellular structures may be displayed on the cell surface or that other lectin-binding structures may be present on cell surfaces. All such lectin-binding structures may be targets for the lectins used in the method of this invention.

Current medical uses of lectins include distinguishing erythrocytes of different blood types (blood typing). More recently, lectins have been used ex-vivo in depleting T cells of patients undergoing bone marrow transplantation.

In the context of this application the term microorganism includes any microscopic organism within the cataegories of algae, bacteria, fungi, protozoa, viruses, and subviral agents.

Among the microorganisms that are bound by certain lectins are infectious organisms such as bacteria, protozoa, and viruses. Lectins may be used to identify such microorganisms in vitro and are also capable of binding to them in vivo, thereby preventing them from infecting living cells. Human disease-causing organisms (and the diseases caused by them) that can be bound by lectins include *Neisseria gonorrhoeae* (gonorrhoea); *Chlamydia trachomatis* (chlamydia, lymphogranuloma venereum); *Treponema pallidum* (syphilis); *Haemophilus ducrei* (chancroid); *Donovania granulomatis* (donovanosis); *Mycoplasma pneumoniae, M. hominis, M. genitalium, Ureaplasma urealyticum* (mycoplasmas); *Shigella flexneri* (shigella); *Salmonella typhi, S. choleraesuis, S. enteritidis* (salmonella); *Campylobacter fetus, C. jejuni* (campylobacter); human immunodeficiency virus HIV-1 and HIV-2 (HIV, AIDS); HTLV-1 (T-lymphotrophic virus type 1); herpes simplex virus type 1 and type 2 (HSV-1 and HSV-2); Epstein-Barr virus; cytomegalovirus; human herpesvirus 6; varicella-zoster virus; human papillomaviruses (many types) (genital warts); molluscum contagiosum (MSV); hepatitis A virus, hepatitis B virus (viral hepatitis); *Trichomoniasis vaginalis* (trichomoniasis); yeasts such as *Candida albicans* (vulvovaginal candidiasis). Other diseases that are transmitted by contact with bodily fluids may also be transmissible by sexual contact and are capable of being prevented by administration of lectins according to this invention. Accordingly, the term sexually transmitted diseases (STD's) is to be interpreted in this application as including any disease that is capable of being transmitted in the course of sexual contact, whether or not the genital organs are the site of the resulting pathology.

Inasmuch as lectins are also capable of agglutinating human sperm and other components of the male ejaculate, and thereby rendering the sperm immobile, intravaginal administration of lectins can also serve as a method of contraception.

According to the invention a dose of lectins adapted to bind and agglutinate pathogenic microorganisms and/or block the recognition sites on target cells is administered to the vagina prior to sexual intercourse. The active ingredients may also include lectins capable of binding and/or inactivating sperm to serve as a contraceptive.

Because of the specificity of lectins for certain microorganisms, it is preferred to administer a mixture of lectins chosen for their properties of agglutinating specific pathogens. It is also according to the invention to administer a mixture of sperm-agglutinating lectins and lectins capable of binding to pathogenic organisms to provide simultaneous contraception and protection against infection.

A representative listing of lectins, the abbreviations by which they are referred to, and their sources is given in Table 1.

TABLE 1

Lectins and Abbreviations

| Lectin | Source |
| --- | --- |
| AAnA | Anguilla anguilla (Eel serum) |
| AAurA | Aleuria aurantia (Orange peel fungus) |
| ABA | Agaricus bisporus (Mushroom) |
| ABrA | Amphicarpanea bracteata (hog-peanut) |
| AL | Hippaestrum hybrid (Amaryllis bulbs) |
| APA | Abrus precatorius (Jequirity bean) |
| BPA | Bauhinia purpurea alba (camel's foot tree) |
| CAA | Caragana arborescens (Siberian pea tree) |
| ConA | Concanavalia ensiformis (Jack bean) |
| CPA | Cicer arietinum (chick pea) |
| CSA | Cytisus scoparius (Scotch broom) |
| DBA | Colichos biflorus (horse gram) |
| DSA | Datura Stramonium (Jimson weed, Thorn apple) |
| ECA | Erythrina crystagalli (Coral tree) |
| ECorA | Erythrina coralldendron (Coral tree) |
| EEA | Euonymus europaeus (spindle tree) |
| DBA | Dolichos biflorus (horse gram) |
| GNA | Galanthus nivalis (Snowdrop bulb) |
| GSA-I/GSA-II | Griffonia simplicifolia |
| HAA | Helix aspersa (Garden snail) |
| HPA | Helix pomatia (Roman or edible snail) |
| JAC (Jacalin) | Artocarpus integrifolia (jackfruit) |
| LAA | Laburnum alpinum |
| LBA | Phaseolus lunatis (also limensis) (Lima bean) |
| LCA (LcH) | Lens culinaris (lentil) |
| LEA | Lycopersicon esculentux (Tomato) |
| LOA | Lathyrus oderaturs (Sweet pea) |
| LTA (LOTUS) | Lotus tetragonolobus (Asparagus pea) |
| MAA | Maackla amurensis (maackla) |
| MPA | Maclura pomifera (Osage orange) |
| NPL (NPA) | Narcissus pseudonarcissus (daffodil) |
| PAA | Phytolacca americana (Pokeweed) |
| PHA (PHA-L) | Phaseolis vulgaris (Red kidney bean) |
| PNA | Arachis hypogaea (Peanut) |
| PSA | Pisum sativum (Pea) |
| PWA | Phytolacca americana (pokeweed) |
| PTAgalactose | Psophocarpus tetagonolobus (winged bean) |
| PTAgalNac | Psophocarpus tetagonolobus (winged bean) |
| RCA-I/RCA-II | Ricinus communis (Castor bean) |
| RPA | Robinia pseudoaccacia (black locust) |
| SBA | Glycine max (Soybean) |
| SJA | Sophora japonica (Japanese pagoda tree) |
| STA | Solanum tuberosum (Potato) |
| TKA | Trichosanthes kinlowii (China gourd) |
| UEA-I/UEA-I1 | Ulex europaeus (Gorse or Furz seeds) |
| VAA | Viscum album (European mistletoe) |
| VFA | Vicia faba (Fava bean) |
| VGA | Vicia graminea |
| VRA | Vigna radiata (mung bean) |
| VSA | Vicia Sativa |
| VVA | Vicia villosa (Hairy vetch) |
| WFA | Wisteria floribunda (Japanese wisteria) |
| WGA | Triticum vulgaris (Wheat germ) |
| suc-WGA | Succinyl WGA |

For example, N. gonorrheae is agglutinated by lectins that bind to N-acetyl-D-glucosamine residues on their surfaces. Such lectins include WGA and STA, which are known to agglutinate all 193 clinical isolates of N. gonorrheae. WGA is effective for such agglutination at a concentration of 3.1 micrograms per milliliter. Other lectins showing some agglutination activity with respect to N. gonorrheae include RCA-I, RCA-II, GSA-I, and SBA.

Certain species of Chlamydia (trachomatis, psittaci, and pneumoniae) are known to be bound by the lectins ConA, DBA, UEA-1, SBA, and PNA. WGA also binds to the receptors on certain cells, thereby blocking infection by C. trachomatis and C. psittaci.

PHA binds to several isolates of H. ducrei, suggesting that N-acetyl-D-glucosamine is present in the cell envelope polysaccharide.

WGA has been found to agglutinate a variety of bacterial cells, including Escherichia coli, Micrococcus luteus, and some types of Staphylococcus aureus. WGA, specific for N-acetyl-D-glucosamine and SBA, specific for N-acetyl-D-galactosamine, are capable of agglutinating the many bacterial species which contain these sugar residues in their cell wall polysaccharides.

Various lectins are capable of binding to certain glycoproteins present in the envelope of HIV virus. For example, ConA has been found to block infection of certain cell lines against infection by HIV in vitro, and conglutinin, a lectin derived from bovine serum, has been found to bind to the HIV envelope precursor protein gp 160, thereby preventing attachment to CD-4 receptors of target cells in vitro. GNA has been found to prevent infection of T-cells by HIV in vitro. Consequently, ConA, GNA and WGA have been found to be effective at preventing infection of target cells by HIV-1 and HIV-2 in vitro. NPL and conglutinin have shown some activity as well.

HPA and ConA have demonstrated efficacy in the prevention of infection of target cells by HSV-1 and HSV-2.

Lectins are also useful in aggregation of sperm. PHA, WGA, STA, ConA, PSA, APA, ECA, ECorA have demonstrated varying degrees of efficacy in agglutination of sperm.

While the lectins discussed above and the organisms against which they are effective are representative of useful lectins according to the invention, it is to be understood that other lectins may be discovered which are active in the binding and agglutination of the pathogens of sexually transmitted diseases, and that the use of such lectins is intended to be included within the scope of the invention.

In determining the amount of lectin to be administered for effective binding and/or agglutination of the pathogenic organisms of STD's, the amount of lectin that might be bound to vaginal tissues and thereby made unavailable for agglutination of pathogens must be considered. In studies on murine vaginal tissue, DBA, LAA, LBA, LCA, LTA, RCA-I, RCA-II, SJA, STA, VGA, WFA have been found not to bind to the tissue at any stage of the estrus cycle. In contrast, ABA, MPA, PHA-E, PHA-L, Suc ConA, and WGA bound strongly to vaginal tissues at all stages of the estrus cycle. CSA, GSA-I, GSA-II, HAA, HPA, JAC, PNA, PAA, SBA, Suc WGA, UEA-I, VFA, and VVA exhibited intermediate degrees of binding to murine vaginal tissues. The amount of lectin to be administered for effective prophylaxis can be determined from the relative binding effect of the various lectins to the pathogen and to the vaginal tissues.

The selection of particular lectins to be administered will depend on the diseases sought to be prevented. It is preferred to administer a mixture of lectins, each selected for best agglutinative efficacy against a particular pathogen.

The lectins may be administered in any fluid or ointment vehicle suitable for topical administration of pharmaceutical compounds. Thus creams, ointments, foams, suppositories, ovules and the like may be formulated in which the selected lectins are dispersed in a non-toxic vehicle suitable for topical and in particular for vaginal administration. Such vehicles include white petrolatum, hydrophilic petrolatum, lanolin emulsions, polyethylene glycols, cocoa butter and the like. Useful vehicles include emollient oils such as water-soluble oils, e.g., liquid polyethylene glycols, which promote complete and uniform distribution of the medicament within the vagina. Representative suitable vehicles include a lubricating jelly comprised of water,propylene glycol, hydroxyethyl cellulose, benzoic acid and sodium hydroxide, a water-soluble oil comprised of water, glycerin, propylene glycol, polyquaternium #5, methyl paraben and propyl paraben; a cream comprised of benzyl alcohol, cet-earyl alcohol, cetyl esters wax, octyldodecanol, polysorbate 60, purified water, and sorbitan monostearate; and a suppository comprised of polyethylene glycol (PEG) 18, PEG-32, PEG-20 stearate, benzethonium chloride, methyl paraben and lactic acid.

According to the invention, the dispersion, suspension, or solution of lectins in the vehicle may be applied to the site of a lesion on the external genitalia, such as the lesions produced by herpes simplex virus type 1 or type 2, chancroid, genital warts, chancre of syphilis, and the like, to prevent the transfer of pathogens. The lectins may also be introduced into the vagina in order to prevent conception or infection by pathogens introduced during sexual intercourse. The amount of lectins to be applied will be an amount that is effective to prevent conception or infection or substantially reduce the risk thereof. The amounts needed to achieve these goals will depend on the effectiveness of the individual lectins, their affinity for the target cell and the like. The effective amounts can be determined by the skilled practitioner by routine experimentation.

Because of their ability to bind pathogenic microorganisms, thereby interfering with their mobility, growth and reproduction, lectins are also useful in therapy of topical infections of the vagina. For those diseases wherein the pathogens grow and reproduce within the lumen of the vagina, administration of lectins, alone or in combination with other antimicrobial materials, can assist in the treatment and cure of the infection.

Because some of the conventional means of administering medications to the vagina have certain drawbacks, as discussed above, it is preferred to incorporate the lectins into a device which will remain in the vagina and dispense the lectins over a prolonged period of time in order to maintain an effective concentration of the lectins in the vagina. Such a device may also be designed to provide a barrier that will prevent the access of pathogenic organisms into the uterus and may also function as a contraceptive device.

The device of the invention is generally a ring of elliptical or circular cross-section made, e.g., from a biocompatible, nontoxic thermoplastic polymer or polymeric open-cell polyurethane. Bonded to one side of the ring or molded integral with it is a web of the same material.

Figure 2:
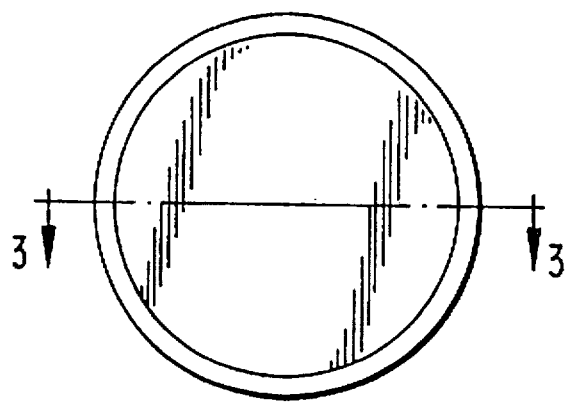
FIG. 2 is a bottom view of the lectin-delivering device of FIG. 1.
Figure 3:
FIG. 3 is a cross section of the lectin-delivering device of FIGS. 1 and 2, taken along the line 3—3.

A device according to the invention having a ring of elliptical cross-section is illustrated in FIGS. 1–3, wherein the reference numerals indicate the same elements in each figure. A ring 102 of generally elliptical cross section constitutes the main structural member of the device and is sized to fit comfortably in the vaginal vault surrounding the cervix. To one side of the ring 102 is fastened a relatively thin web 104, preferably made of the same material as the ring. In some embodiments the web may be molded integrally with the ring.

Figure 4:
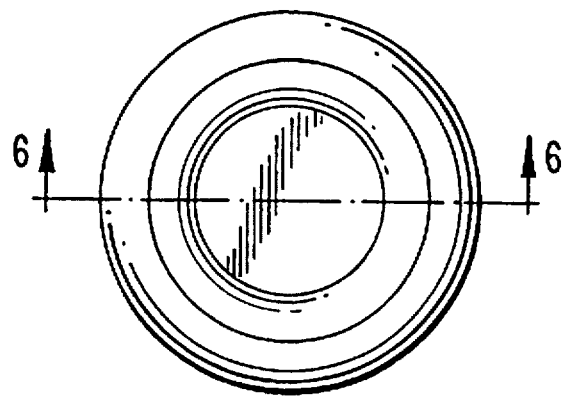
FIG. 4 is a top plan view of another embodiment of the lectin-delivering device of this invention.
Figure 5:
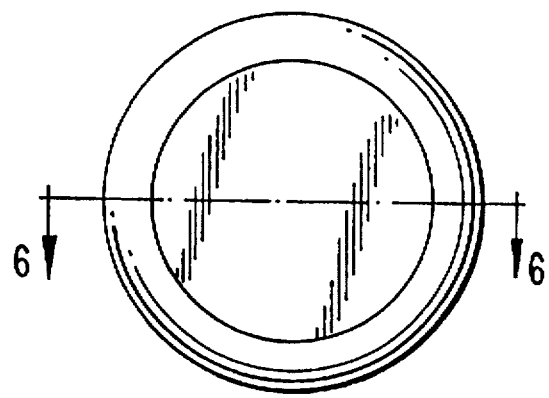
FIG. 5 is a bottom view of the lectin-delivering device of FIG. 4.
Figure 6:
FIG. 6 is a cross section of the lectin-delivering device of FIGS. 4 and 5, taken along the line 6—6.

FIGS. 4–6 illustrate another embodiment of the invention wherein a ring 202, of generally circular cross section, carries a thin web 204 spanning the central aperture on one side of the ring.

The device may be manufactured from any material that has been shown to be biocompatible with the environment of the vagina and to be capable of holding lectins within its bulk and releasing them slowly to the surrounding environment. Several materials suitable for this function are already known from the vaginal devices already in use or disclosed in the technical literature. Consequently, the skilled practitioner can easily select a suitable material from which to make the device of this invention. The lectins may also be incorporated into a thin flexible coating, placed on the ring or web or both, and designed to release the lectins therefrom over a period of time, e.g., by diffusion out of the coating or by gradual erosion and dissolution of the coating in the vaginal environment.

The device of the invention is designed to deliver one or more lectins locally in the vagina for:

1) contraception, by binding to the glycoproteins, glycolipids and other glycoconjugates on the surface of sperm and by binding to the glycoproteins, glycolipids, and other glycoconjugates in the seminal fluid, thereby creating an ejaculate with significantly greater viscosity, and thereby preventing sperm from exiting the ejaculate;

2) prophylaxis against various sexually transmitted diseases by binding to the glycoproteins, glycolipids, and other glycoconjugates on the surface of the bacterial agent or viral coat of the virus and the glycoproteins, glycolipids, and other glycoconjugates in the seminal fluid thereby preventing the infectious agent from reaching the target tissue;

3) prophylaxis against various sexually transmitted diseases by binding to the glycoproteins, glycolipids and other glycoconjugate receptor sites on the vaginal stratified squamous epithelium and cervical columnar epithelium, whereby the recognition sites for attack by pathogens are blocked or concealed; and 4) treatment of topical infections of the vagina by interfering with the growth and reproduction of the pathogenic microorganism, thereby hindering their ability to infect healthy cells.

The device of the invention also operates by providing a physical barrier to the direct deposition of ejaculate on the cervix. This design assures that the concentration of protective lectins in the cervical region will not be diluted and overwhelmed by the ejaculate. Rather, the sperm and the pathogens present in the ejaculate can only reach the cervical region gradually by diffusion and transport around the outside of the peripheral ring of the device. This slow transport of the sperm and pathogens from the ejaculate to the cervical region assures that the lectins will have an opportunity to bind to all appropriate constituents of the ejaculate. The presence of the lectins, which will coagulate and inhibit the transport of sperm and pathogens, makes it unnecessary to have a device that fits tightly either around the cervix or against the wall of the vagina.

Accordingly, the device of the invention has several advantages over the vaginal medication and contraceptive devices currently available:

1) It is easily inserted and comfortable to use.

2) Because of its position in the top of the vaginal canal, it ensures that the lectins are carried down through the vagina.

3) Since it is placed next to the cervix it can also deliver lectins targeted to the cervix.

4) Gradual release of lectins provides a more consistent delivery over time, thus ensuring more efficient treatment.

EXAMPLE 1

This example illustrates the utility of various lectins in binding to certain microorganisms and to seminal plasma, sperm, human serum and cervical mucus.

The efficacy of binding of various lectins to human sperm and seminal plasma and cervical mucus, an indicator of the effectiveness of such materials as vaginally-applied contraceptives, was investigated in vitro by the following procedures. Similarly the efficacy of lectin binding to *Neisseria gonorrhoeae*, the pathogen responsible for gonorrhoea, was investigated by the following in vitro procedures. Such binding efficacy is an indication of the capability of such lectins to bind the pathogen and prevent infection when used intravaginally as a prophylactic material.

Growth of bacteria: A cervical isolate of *Chlamydia trachomatis* serovar G ATCC VR-878 was grown in McCoy cell monolayers in the presence of 1 μg of cycloheximide per ml. The culture medium was 90% Eagle's minimum essential medium-10% fetal calf serum-10 mM HEPES (pH 7.3) supplemented with 100 μg of vancomycin per ml. Elementary bodies were purified by differential centrifugation followed by density gradient centrifugation In Percoll as described by Newhall et al. (Newhall, W. J., Baheiger, B.and Jones, R. B. 1982, Analysis of the human serological response to the proteins of Chlamydia trachomatis, Infection Immunity 38: 1181–1189). The purified elementary bodies were washed twice in 10 mM HEPES-145 mM NaCl (pH 7.4) and resuspended in bicarbonate buffer (100 mM $NaHCO_3$ containing 0.01% $NaN_3$, pH 9.5). The density of elementary bodies was adjusted to a McFarland No. 2 standard using the same buffer. *Neisseria gonorrhoeae* ATCC 19424 were grown on chocolate agar plates for 48–72 hrs at 37° C. in a $CO_2$ incubator (5% $CO_2$ and 80% humidity) and were harvested by scraping bacteria from the agar surface and resuspending the cells in sterile phosphate buffered saline. The cells were washed three times by centrifugation at 5000×g and resuspended in bicarbonate buffer, the density of which was adjusted to a McFarland No. 2 standard (optical density as measured by a spectrometer –0.4 at 650 nm). The cells were stored on ice prior to immediately testing in the lectin binding assay. *Lactobacillus jensenii* ATCC 25258 was grown 48–72 hrs. at 37° C. in a shaking (incubator in MRS broth at pH 5.5 containing 2% glucose. After incubation, cells were centrifuged at 5000×g for 10 min and washed twice in phosphate buffered saline, and the density was adjusted to a McFarland No. 2 standard with bicarbonate buffer. *Haemophilus ducreyi* was grown on chocolate agar plates for 72 hrs in a $CO_2$ incubator (10% $CO_2$ and 80% humidity) t 31° C. Bacteria were harvested by scraping bacteria from the agar surface and resuspending the cells in sterile phosphate buffered saline. The cells were washed three times by centrifugation at 500×g, resuspended in bicarbonate buffer and the cell density adjusted to a McFarland No.2 standard. The cells were stored on ice prior to immediately testing in the lectin binding assay.

Lectin Binding Assay: Biotinylated lectins were reconstituted in phosphate buffered saline (10 mM sodium phosphate-150 mM NaCl, pH 7.2) and stored in a freezer at –70° C. until used. Microtiter plates washed with 95% ethanol and dried were coated with bacteria. (*Chlamydia trachomatis* or *Neisseria gonorrhoeae* or *Haemophilus ducryei* or *Lactobacillus Jensenii*) by adding 200 μl of a bacterial suspension (in bicarbonate buffer) to each well and incubating overnight at room temperature. Wells coated with bacteria were washed three times In either sodium acetate buffered saline, pH 4.0, containing 0.1% Tween detergent (ABST) or phosphate buffered saline containing 0.1% Tween (PBST). Lectins defrosted at room temperature were diluted in each buffer, and 100 μl of various lectins was added to bacteria-coated wells at a fInal concentration of 50 μg/ml. After incubation in a humid chamber at room temperature for 2 hours, wells were washed three times with either ABST or PBST followed by the addition to each well of 100 μl of alkaline phosphatase streptavidin (10 μg/ml). After incubation for 1 hour at room temperature, wells were washed three times with ABST or PBST and 100 μl of freshly prepared p-nitrophenylphosphate (1 mg/ml) in 0.1M Tris buffer-0.15M NaCl was added and color development was quantified with a spectrophotometer at 405 nm.

Cervical Mucus: A sample of cervical mucus was obtained from a healthy donor and the gel phase separated by centrifugation. The pellet was washed three times by centrifugation and the mucin stabilized and alkylated before dialysis against a low ionic strength, pH 8.0 buffer. The cervical mucus was bound to flat-bottomed plates by incubating in bicarbonate coating buffer at 4° C. overnight. The plates were washed to remove unbound ligand. Biotinylated lectins were serially diluted across the plates in the wash buffer and the plates incubated at room temperature for 2 hrs. Unbound lectin was removed by washing, and the bound lectins were tagged by incubating with streptavidin-alkaline. phosphatase at room temperature for 1 hr. Unbound streptavidin-alkaline phosphatase was removed by washing and the assay completed by adding freshly prepared p-nitrophenylphosphate (1 mg/ml) in 0.1M Tris buffer-0.15M NaCl) and monitoring the rate of color production.

Seminal Plasma and Sperm: A sample of ejaculate was donated by a healthy donor and the seminal plasma (supernatant) removed by centrifugation and frozen at –20° C. The binding assay was performed in the same way as for cervical mucus.

The sperm pellet resulting from centrifugation of the ejaculate was washed twice and total sperm count determined using a hemocytometer. Sperm were added to plates, left to settle at room temperature for 2 hrs. and fixed using glutaraldehyde. The plates were then washed and unbound sites blocked with protein solution and stored at +4° C. until use. The remainder of the binding assay was performed in the same way as for cervical mucus and seminal plasma.

Serum: A sample of blood was collected from a healthy donor, the serum separated by centrifugation and stored at –20° C. The binding assay was performed in the same way as for cervical mucus and seminal fluid.

Analysis of data: Sigma Plot was used for graphing and curve fitting of binding plots. Velocity of the color-forming reaction versus concentration of lectin added was plotted. Binding curves were fitted to the hyperbolic equation $f(x)=ax/(b+x)$ where "x" is the concentration of lectin, "f(x)" is the rate of reaction measured by change in optical density (OD) of the reaction solution per unit time, "a" is the asymptotic value of maximum reaction velocity measured as change in optical density per minute (represented in the following tables as $m_{OD}$/min) and "b" is the concentration of lectin where half of maximum binding occurs (represented in the following tables as $[Lectin]_{1/2\ max}$). The binding "quotient" is defined as a/b.

The data for lectin binding to sperm, seminal plasma, cervical mucus, human serum, *Neisseria gonorrhoeae,* and *Lactobacillus jensenii* are summarized in the following tables.

TABLE 2

SUMMARY OF BINDING DATA

| Lectin | Sperm | Seminal Plasma | QUOTIENT Cervical Mucus | Human Serum |
|---|---|---|---|---|
| ABA | WB | 0.44 | WB | WB |
| AL | NB | NB | NB | NB |
| BPA | 0.60 | 0.86 | 20.76 | WB |
| CAA | 0.46 | 1.04 | 7.82 | WB |
| ConA | 2.59 | 2.68 | 1.11 | 3.29 |
| CPA | WB | WB | WB | WB |
| CSA | WB | 0.30 | 7.30 | WB |
| DBA | WB | WB | WB | WB |
| DSA | 1.09 | WB | WB | WB |
| ECA | WB | WB | WB | WB |
| EEA | NB | NB | 0.39 | NB |
| GNA | 0.36 | 0.58 | 0.24 | WB |
| GSA-I/GSA-II | WB | WB | WB | WB |
| HAA | NB | WB | WB | WB |
| Jacalin | 3.43 | 11.63 | 21.55 | 8.93 |
| LAA | NB | 0.57 | WB | WB |
| LBA | WB | WB | WB | WB |
| LcH | 7.26 | 2.58 | 8.64 | 1.60 |
| LES | WB | WB | WB | WB |
| LOTUS | NB | 0.94 | 4.13 | |
| MAA | NB | WB | WB | NB |
| MPA | 2.29 | 3.17 | 13.8 | 1.18 |
| NPA | NB | NB | NB | NB |
| PWA | WB | NB | NB | NB |
| PHA-L | WB | WB | WB | NB |
| PNA | WB | WB | 7.25 | NB |
| PSA | 3.44 | 2.70 | 14.5 | 1.12 |
| PTAgalactose | NB | WB | 1.31 | WB |
| PTAgalNacnb | NB | NB | 1.39 | WB |
| RPA | 1.28 | 0.84 | 0.45 | WB |
| SBA | NB | WB | WB | NB |
| SJA | NB | WB | WB | NB |
| STA | NB | WB | WB | NB |
| sWGA | 1.32 | 7.50 | WB | WB |
| TKA | WB | 0.87 | WB | WB |
| UEA-1 | WB | WB | 14.72 | WB |
| VPA | WB | 2.78 | 5.21 | 2.02 |
| VRA | WB | 3.35 | WB | WB |
| VVA | N/A | 0.81 | WB | WB |
| WFA | 2.48 | 1.96 | 26.24 | WB |
| WGA | 19.38 | 4.87 | 12.77 | 1.13 |

Notes
1. N/A - not available
2. NB - no binding
3. WB - weak binding

TABLE 3

LECTIN BINDING TO SPERM

| Lectin | Max ($m_{OD}$/min) | [Lectin]$_{1/2\ Max}$ (μg/ml) | Quotient |
|---|---|---|---|
| WGA | 155 | 8 | 19.38 |
| LcH | 196 | 27 | 7.26 |
| PSA | 141 | 41 | 3.44 |
| Jacalin | 103 | 30 | 3.43 |
| ConA | 57 | 22 | 2.59 |
| WFA | 67 | 27 | 2.48 |
| MPA | 48 | 21 | 2.29 |
| sWGA | 41 | 31 | 1.32 |
| RPA | 120 | 94 | 1.28 |
| DSA | 63 | 58 | 1.09 |
| BPA | 67 | 112 | 0.60 |
| CAA | 33 | 71 | 0.46 |
| GNA | 27 | 74 | 0.36 |

TABLE 4

LECTIN BINDING TO SEMINAL PLASMA

| Lectin | Max ($m_{OD}$/min) | [Lectin]$_{1/2\ Max}$ ('Lglml) | Quotient |
|---|---|---|---|
| Jacalin | 93 | 8 | 11.63 |
| sWGA | 45 | 6 | 7.50 |
| WGA | 112 | 23 | 4.87 |
| VRA | 208 | 62 | 3.35 |
| MPA | 57 | 18 | 3.17 |
| VFA | 125 | 45 | 2.7 |
| PSA | 100 | 37 | 2.70 |
| ConA | 51 | 19 | 2.68 |
| LcH | 147 | 57 | 2.58 |
| WFA | 49 | 25 | 1.96 |
| CAA | 51 | 49 | 1.04 |
| LOTUS | 32 | 34 | 0.94 |
| BPA | 64 | 74 | 0.86 |
| RPA | 56 | 64 | 0.88 |
| VVA | 25 | 31 | 0.81 |
| GNA | 38 | 65 | 0.58 |
| TKA | 39 | 45 | 0.87 |
| LAA | 37 | 65 | 0.57 |
| ADA | | | 0.44 |
| CSA | 25 | 82 | 0.30 |

TABLE 5

LECTIN BINDING TO CERVICAL MUCUS

| Lectin | Max ($m_{OD}$/min) | [Lectin]$_{1/2\ Max}$ (μg/ml) | Quotient |
|---|---|---|---|
| WFA | 656 | 25 | 26.24 |
| Jacalin | 237 | 11 | 21.55 |
| BPA | 353 | 17 | 20.76 |
| UEA-1 | 265 | 18 | 14.72 |
| PSA | 58 | 4 | 14.50 |
| MPA | 138 | 10 | 13.80 |
| WGA | 562 | 44 | 12.77 |
| LcH | 121 | 14 | 8.64 |
| CAA | 352 | 45 | 7.82 |
| CSA | 445 | 61 | 7.30 |
| PNA | 174 | 24 | 7.25 |
| VFA | 203 | 39 | 5.21 |
| LOTUS | 194 | 47 | 4.13 |
| PTAgalNac | 110 | 79 | 1.39 |
| PTAgalactose | 113 | 86 | 1.31 |
| ConA | 41 | 37 | 1.11 |
| RPA | 25 | 56 | 0.45 |
| EEA | 27 | 70 | 0.39 |
| GNA | 13 | 55 | 0.24 |

TABLE 6

LECTIN BINDING TO HUHAN SERUM

| Lectin | Max ($m_{OD}$/min) | [Lectin]$_{1/2\ Max}$ (μg/ml) | Quotient |
|---|---|---|---|
| Jacalin | 134 | 15 | 8.93 |
| ConA | 79 | 24 | 3.29 |
| VFA | 107 | 53 | 2.02 |
| LcH | 123 | 77 | 1.60 |
| MPA | 40 | 34 | 1.18 |
| WGA | 160 | 142 | 1.13 |
| PSA | 84 | 75 | 1.12 |

TABLE 7

LECTIN BINDING TO NEISSERIA GONORRHOEAE pH4

| Lectin | Max ($m_{OD}$/min) | [Lectin]$_{1/2\,Max}$ (µg/ml) | Quotient |
|---|---|---|---|
| BPA | 1190 | 82 | 14.51 |
| CPA | 80 | 33 | 2.42 |
| CSA | 560 | 7 | 80.00 |
| GNA | 294 | 18 | 16.33 |
| LAA | 176 | 42 | 4.19 |
| LBA | 275 | 14 | 19.64 |
| LCH | 213 | 176 | 1.21 |
| LEA | 106 | 7 | 14.29 |
| MAA | 235 | 56 | 4.20 |
| MPA | 159 | 8 | 31.80 |
| NPA | 299 | 38 | 7.87 |
| PSA | 55 | 13 | 4.23 |
| RPA | 233 | 10 | 23.30 |
| SBA | 414 | 5 | 51.75 |
| STA | 194 | 24 | 7.57 |
| sWGA | 49 | 0.50 | 90.00 |
| TKA | 178 | 55 | 3.24 |
| VVA | 411 | 3 | 137.00 |
| WFA | 331 | 3 | 110.33 |
| WGA | 125 | 0.78 | 160.26 |

TABLE 8

LECTIN BINDING TO LACTOBACILLUS JENSENII

| Lectin | Max ($m_{OD}$/min) | [Lectin]$_{1/2\,Max}$ (µg/ml) | Quotient |
|---|---|---|---|
| ABA | 216 | 2 | 108.00 |
| BPA | 557 | 57 | 9.77 |
| GNA | 405 | 12 | 33.75 |
| Jacalin | 148 | 7 | 21.14 |
| LBA | 334 | 15 | 22.27 |
| RPA | 177 | 55 | 3.22 |
| SBA | 523 | 63 | 8.30 |
| WFA | 464 | 23 | 20.17 |
| STA | 140 | 19 | 7.37 |
| LEA | 45 | 82 | 0.55 |
| DSA | 26 | 80 | 0.33 |
| MPA | 2047 | 328 | 6.24 |
| ConA | 301 | 7 | 43.00 |
| sWGA | 96 | 64 | 1.50 |
| LAA | 136 | 17 | 8.00 |
| CSA | 624 | 387 | 1.61 |
| NPA | 425 | 36 | 11.81 |
| VVA | 260 | 33 | 7.88 |

In the above tables the affinity of the lectin for a particular substrate is inversely proportional to the maximum velocity of the color-forming reaction. Consequently, those lectins having a smaller b value ([lectin]$_{1/2\,max}$) bind more firmly to the substrate. A high binding efficacy (low $m_{OD}$/min) is preferable for binding to sperm or seminal plasma for contraceptive purposes or to a pathogen, such as *Neisseria gonorrhoeae*, whose infections activity is to be inhibited. However, it must be recognized that some microorganisms of the vaginal flora, e.g., *Lactobacillus jensenii*, are desirable and may even provide some protection against pathogenic organisms. Accordingly, if possible, it is desirable to select a lectin for contraception and/or prophylaxis against sexually transmitted diseases that combines great binding affinity for the constituents of the male ejaculate or for a pathogenic microorganism, but has a lesser, preferably minimal, binding affinity for beneficial vaginal flora. A skilled practitioner may select the most efficacious lectins by consulting the data provided in the tables of this example.

EXAMPLE 2

This example illustrates the effectiveness of lectins in inhibiting the infective activity of *Chlamydia trachomatis*.

*Chlamydia trachomatis* serovar G was cultured as described in Example 1. Lyophilized lectins were reconstituted in phosphate buffered saline (PBS) to a concentration of 1 mg/ml and frozen at −20° C. The lectins were prepared for testing in the *Chlamydia trachomatis* inactivation assay by diluting them in McCoy growth medium (MEM) to appropriate concentrations. *Chlamydia trachomatis* serovar G was added to the diluted lectins and the mixture was incubated for 1 hour at 37° C. After incubation, the Chlamydia-lectin mixture was added to McCoy cells in 15×45 mm shell vials and centrifuged at 3500 xg for 60 minutes at 37° C. Following centrifugation, the medium in the vials was removed and 1 ml of Chlamydia overlay medium (with cycloheximide ) was added to each vial. The vials were incubated for 42–43 hours and the cells were then fixed and stained for *Chlamydia trachomatis* using Syva Microtrak™ *Chlamydia trachomatis* culture confirmation reagent.

Samples of the infected cell culture were then examined under the microscope and evaluated for the effect of the lectin on the infectivity of the microorganism. Table 9 shows the number of Chlamydia trachomatis inclusions per 160× microscopic field on a 12 mm circular glass coverslip as a percentage of a positive control sample which was not exposed to any lectins. WGA (118%) and ConA (121%) show enhanced infectivity of *Chlamydia trachomatis* serovar G in having more inclusions per 160×field than the positive control which had not been exposed to any lectins. In contrast, exposure to Jacalin shows significantly reduced infectivity of *Chlamydia trachomatis* serovar G as evidenced by the 65% reduction in the number of inclusions per 160×field (35% of the positive control value).

TABLE 9

| Lectin | Concentration | Infectivity |
|---|---|---|
| ABA | 150 | 59 |
| TKA | 150 | 80 |
| WGA | 50 | 118 |
| DSA | 50 | 75 |
| WFA | 150 | 48 |
| VFA | 150 | 61 |
| ConA | 150 | 121 |
| Jacalin | 150 | 35 |
| MPA | 150 | 55 |

EXAMPLE 3

This example illustrates the effectiveness of lectins in blocking the infectivity of human immunodeficiency viruses Type 1 and 2 (HIV-1/HIV-2).

The effect of lectins on the infectivity of HIV-1 and HIV-2 toward human lymphocytes was investigated in vitro by a standard technique (Balzarini et al. 1991, *Antimicrobial Agents and Chemotherapy*, March 1991, pages 410–416) wherein the toxicity of the lectins toward the infected cells was determined (human T-lymphocytes CEM/0) and also the ability of the lectins to block the fusion of infected cells (HUT-78/HIV-1(III$_B$)) with other cells (MOLT/4 clone 8). The results of these tests are set forth in Tables 10 and 11 below. The results are expressed in terms of the concentration of lectins required to reduce by 50% the number of viable cells in the virus-infected cell cultures (EC$_{50}$) and in the control cell cultures (mock-infected) (CC$_{50}$), respectively.

TABLE 10

Anti-HIV-1 and -HIV-2 Activity and cytotoxicity of Lectins in Human T-Lymphocyte (CEM/0) Cells

| Compound | EC$_{50}$$^a$ (μg/ml) HIV-1 | HIV-2 | CC$_{50}$$^b$ (μg/ml) |
|---|---|---|---|
| ABA | >100->100 | >100->100 | 83-62 |
|  | >100 | >100 | 73 ± 15 |
| CAA | >100->100 | >100->100 | 140->200 |
|  | >100 | >100 | >140 |
| ConA | 2.4-0.8-1.4 | 1.8-0.8-2.4 | 20-19 |
|  | 1.5 ± 0.79 | 1.4 ± 0.77 | 20 ± 0.71 |
| CPA | >100->100->100 | >100->100->100 | >200->200->200 |
|  | >100 | >100 | >200 |
| CsA | >100->100->100 | >100->100->100 | >200->200->200 |
|  | >100 | >100 | >200 |
| DSA | >20 | >20 | >10.5 |
| ECA | >100->100 | >100->100 | 12-15 |
|  | >100 | >100 | 14 ± 2.5 |
| EEA | >0.16->0.16 | >0.16->0.16 | 0.47-0.53 |
|  | >0.16 | >0.16 | 0.50 ± 0.04 |
| GSA-I | >100->100 | >100->100 | >200->200 |
|  | >100 | >100 | >200 |
| GSA-II | >100->100->100 | >100->100->100 | 90->200->200 |
|  | >100 | >100 | >90 |
| HAA | 20-9 | 11.5-11.5 | 9.7-18 |
|  | 15 ± 7.8 | 11.5 | 14 ± 5.9 |
| JAC | >20->20 | >20->20 | 16-27 |
|  | >20 | >20 | 22 ± 7.4 |
| LAA | >100->100 | >100->100 | >200->200 |
|  | >100 | >100 | >200 |
| LBA | >100->100 | >100->100 | >200->200 |
|  | >100 | >100 | >200 |
| LCH | 9-4-20 | >100->100->100 | 17-17-12 |
|  | 11 ± 8.2 | >100 | 15 ± 2.9 |
| LEA | >100->100 | >100->100 | >200->200 |
|  | >100 | >100 | >200 |
| Lotus | >100->100 | >100->100 | 90->200->200 |
|  | >100 | >100 | >90 |
| MPA | >0.8->4 | >0.8->4 | 6.8-11 |
|  |  | >0.8 | 8.9 ± 3.0 |
| PAA | >100->100 | >100-58 | >200->200 |
|  | >100 | >58 | >140 |
| PHA-L | 11.5-11.5-45 | >100->100>100 | 11-23 |
|  | 23 ± 19 | >100 | 17 ± 8.5 |
| PNA | >100->20->20 | >100->20->20 | 95-80 |
|  | >20 | >20 | 88 ± 11 |
| PSA | 20-9-20-45 | 45-100-100 | 25-17 |
|  | 16 ± 6.4 | 82 ± 32 | 21 ± 5.7 |
| PTAgal | >100->100->100 | >100->100->100 | >200->200 |
|  | >100 | >100 | >200 |
| PTAgalNac | >100->100 | >100->100 | >200->200 |
|  | >100 | >100 | >200 |
| SJA | >100->100 | >100->100 | >200->200 |
|  | >100 | >100 | >200 |
| sWGA | >100->100 | >100->100 | >200->200 |
|  | >100 | >100 | >200 |
| TKA | >100->100 | >100->100 | 100-95 |
|  | >100 | >100 | 98 ± 3.5 |
| UEA-1 | >100->100 | >100->100 | >200->200 |
|  | >100 | >100 | >200 |
| VFA | 9-34-38 | >100->100-100 | 120-77-95 |
|  | 34 ± 25 | >100 | 97 ± 22 |
| VVA | >100->100 | >100->100 | >200->200 |
|  | >100 | >100 | >200 |
| WFA | >100->100 | >100->100 | >200->200 |
|  | >100 | >100 | >200 |
| WGA | 11.5-20->20 | 9->20-20 | 11.5-15 |
|  | >16 ± 6.0 | >15 ± 7.8 | 13 ± 2.5 |

$^a$- Effective concentration or concentration required to protect CEM cells against the cytopathogenicity of HIV by 50%.
$^b$- Cytotoxic concentration or concentration required to reduce CEM cell viability by 50%.
*Cluster formation of the cells after 4 days incubation with the compound.

TABLE 11

Inhibitory Effect of Lectins on Giant Cell Formation Between HUT-78/HIV-1(III$_B$) and MOLT/4 clone 8 cells

| Compound | EC$_{50}$ (μg/ml) Individual Values | Average |
|---|---|---|
| ABA | >100->100 | >100 |
| CAA | >100->100 | >100 |
| ConA | 1.7-9 | 5.4 > 5.2 |
| CPA | >100->100 | >100 |
| CSA | >100->100 | >100 |
| ECA | >100->100 | >100 |
| EEA | >4->4 | >4 |
| GSA-I | >100->100 | >100 |
| GSA-II | >100->100 | >100 |
| HAA | >100->100 | >100 |
| JAC | >100->100 | >100 |
| LAA | >100->100 | >100 |
| LBA | >100->100 | >100 |
| LCH | 45-45 | 45 |
| LEA | >100->100 | >100 |
| Lotus | >100->100 | >100 |
| MPA | >100->100 | >100 |
| PAA | >100->100 | >100 |
| PHA-L | 44-12-44 | 33 ± 18 |
| PNA | >100->100 | >100 |
| PSA | 45-58-58 | 54 ± 7.5 |
| PTAgal | >100->100 | >100 |
| PTAgalNac | >100->100 | >100 |
| SJA | >100->100 | >100 |
| sWGA | >100->100 | >100 |
| TKA | >100->100 | >100 |
| UEA-I | >100->100 | >100 |
| UFA | >100->100 | >100 |
| VVA | >100->100 | >100 |
| WFA | >100->100 | >100 |
| WGA | 20->4 | >20 |

*Cluster formation of the cells after 1 day incubation with the compound

The invention having now been fully described, it should be understood that it may be embodied in other specific forms or variations without departing from its spirit or essential characteristics. Accordingly, the embodiments described above are to be considered in all respects as illustrative and not restrictive, the scope of the invention being indicated by the appended claims rather than by the foregoing description, and all changes which come within the meaning and range of equivalency of the claims are intended to be embraced therein.

We claim:

1. A method of contraception comprising administering to the vagina an amount of a composition containing at least one lectin capable of agglutinating sperm or other components of male ejaculate sufficient to render said sperm incapable of fertilization, said lectin being dispersed in a biocompatible non-toxic vehicle.

2. The method of claim 1 wherein a plurality of lectins is administered.

3. The method of claim 1 wherein said lectin is selected from the group consisting of WGA, LcH, PSA, Jacalin, ConA, WFA, MPA, sWGA, RPA, DSA, BPA, CAA, GNA, VRA, VFA, LOTUS, VVA, TKA, LAA, ABA, CSA, UEA-1, PNA, PTAgalNac, PTAgalactose, and EEA.

4. The method of claim 3 wherein a plurality of lectins is administered.

* * * * *